Figure 3:
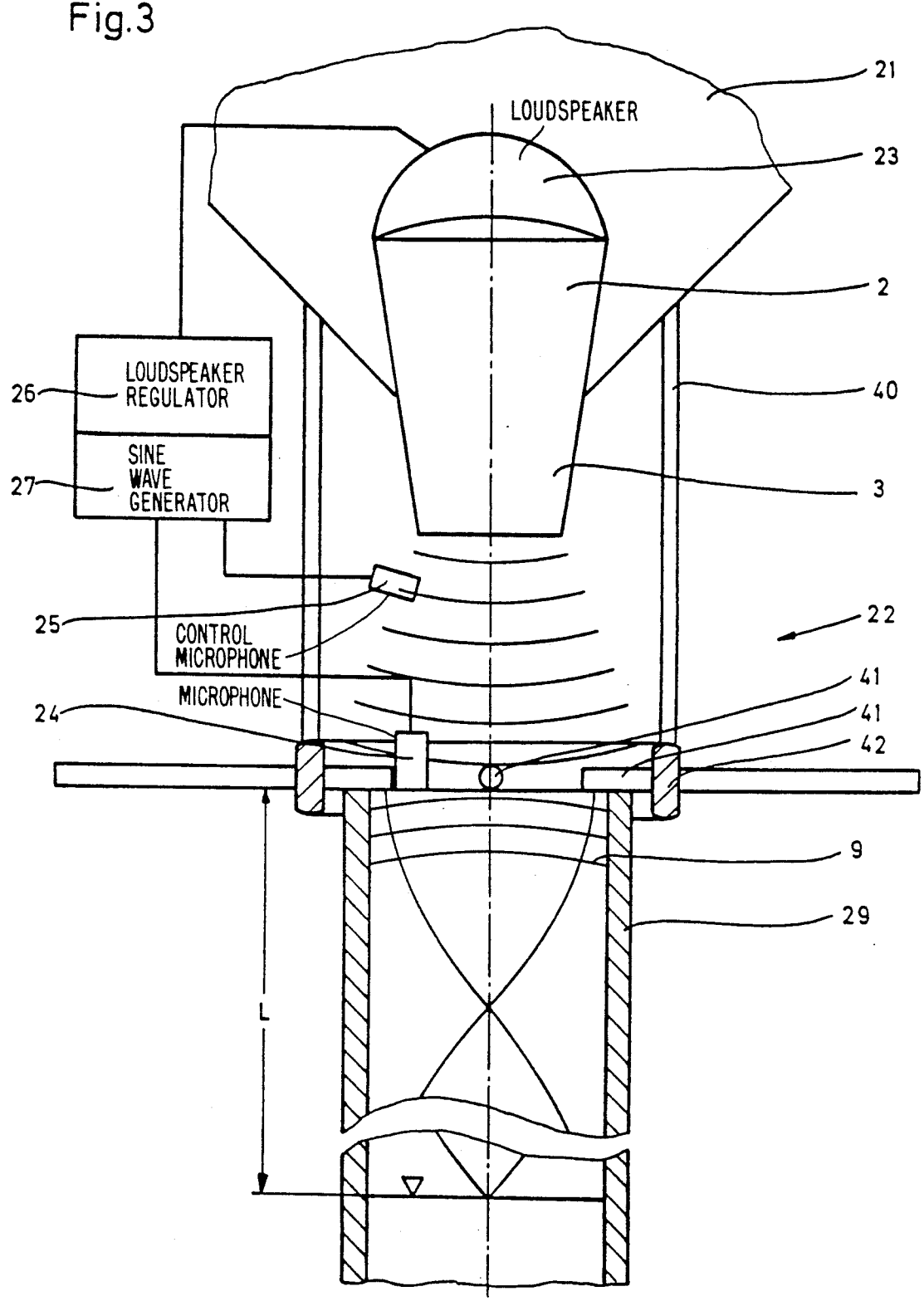

United States Patent [19]

Hrdlicka et al.

[11] Patent Number: 5,184,512
[45] Date of Patent: Feb. 9, 1993

[54] MEASURING THE LENGTH OF A COLUMN OF FLUID IN A TUBE

[76] Inventors: Armin W. Hrdlicka,
Anzengruberstrasse 34/4, A-9020
Klagenfurt; Wolfgang Pribyl,
Schiessstattgasse 14b, A-8010 Graz;
Hermann Schuster, Hochleitenweg,
A-8061 St. Radegund; Klaus Loibner,
Brunnbodensiedlung 4, A-8101
Gratkorn; Harald Koffler,
Strassgangerstrasse 15, A-8020 Graz,
all of Austria

[21] Appl. No.: 801,892

[22] Filed: Dec. 3, 1991

Related U.S. Application Data

[62] Division of Ser. No. 462,032, Jan. 8, 1990, Pat. No. 5,099,691.

[30] Foreign Application Priority Data

Jan. 16, 1989 [AT] Austria ................................. 68/89
Oct. 16, 1989 [AT] Austria ............................... 2375/89

[51] Int. Cl.$^5$ ................................................ G01N 9/24
[52] U.S. Cl. ................................... 73/584; 73/290 V
[58] Field of Search ............... 73/597, 587, 592, 19.03, 73/290 V, 579

[56] References Cited

U.S. PATENT DOCUMENTS

| 3,237,445 | 3/1966 | Wood | 73/579 |
| 3,854,327 | 12/1974 | Felix | 73/584 |
| 4,704,902 | 11/1987 | Doshi | 73/290 V |
| 4,811,595 | 3/1989 | Marcianiak et al. | 73/290 V |
| 4,858,460 | 8/1989 | Schohl et al. | 73/19.03 |

FOREIGN PATENT DOCUMENTS

| 1467228 | 1/1967 | France . |
| 2185095 | 12/1973 | France . |
| 842241 | 7/1960 | United Kingdom . |

OTHER PUBLICATIONS

"11.Laufzeitverfahren", *Werkstoffprufung mit Ultraschall,* 1980, By J. Krauthkramer et al., pp. 265–267.
"Kabelmesskoffer", *Gerbrauchsanweisung,* 16-2, By T. Meko, pp. 2–16 (date unknown).
"Ein Lehrbuch Zum Gebrauch neben Vorlesungen", *PHYSIK,* By H. Vogel, pp. 171–173 (date unknown).
"Besonderheiten der Fehlerortung bei Starkstromkabeln", pp. 127–130 (date unknown).

*Primary Examiner*—Louis Arana
*Attorney, Agent, or Firm*—Young & Thompson

[57] ABSTRACT

The length of a column of a gaseous or liquid substance or of a solid bar is determined by generating a standing wave of known frequency, wavelength and/or wave velocity in the column or in the bar. The wave frequency is varied until at least two consecutive maxima (antinodes), two consecutive minima (nodes) or a minimum following a maximum of the amplitude of the standing wave have been detected. The length of the column of medium at known frequency and wave velocity of the standing wave generated in that column is computed from the equation $$L = c/[2(f_n - f_{n-1})] \qquad (1).$$

where L is the length of the column of medium, c is the wave velocity, $f_n$ is the frequency of the nth maximum and $f_{n-1}$ the frequency of the (n−1)th maximum. Apparatus for implementing the method comprises a loudspeaker 1 mounted in a resonance chamber 2 with a tubular acoustic exit aperture 3. The resonance chamber 2 is mounted by a spacer 4 a distance from the pipe 6 containing the column of gaseous or liquid substance whose length must be determined. The spacer 4 also supports the receiving microphone 7. To keep the acoustic pressure constant over the frequency-/wavelength range in the resonance chamber, the acoustic volume in this resonance chamber is kept constant by a regulator unit 11 with a control microphone 10.

7 Claims, 5 Drawing Sheets

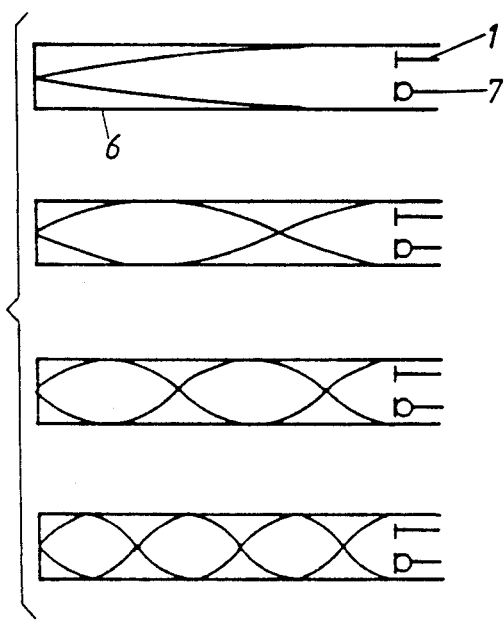
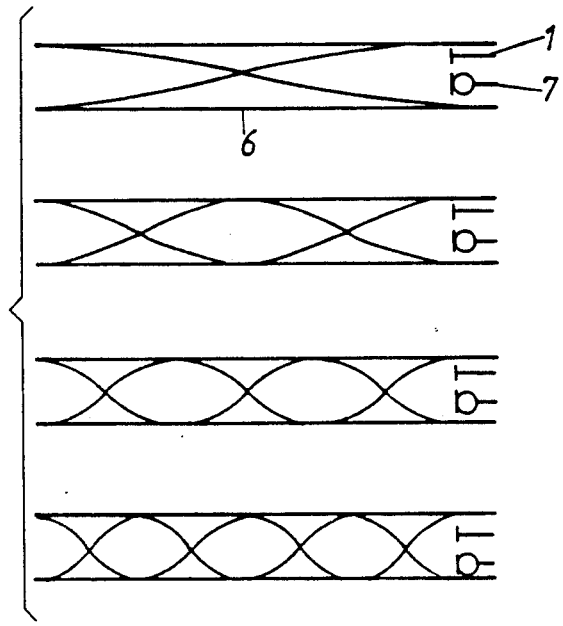
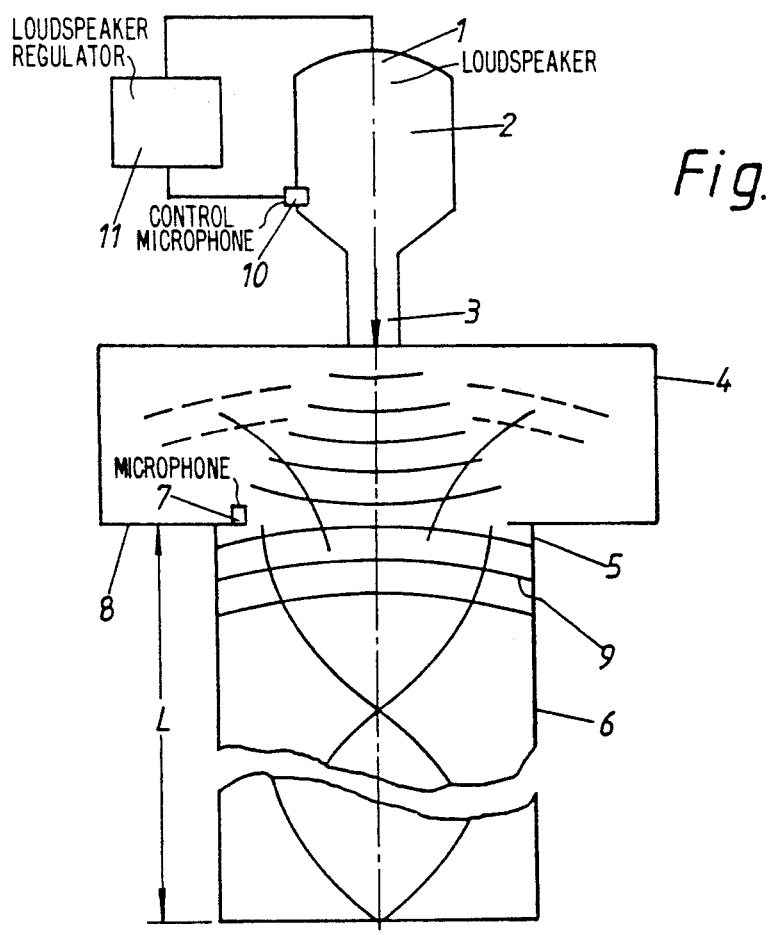

MEASURING THE LENGTH OF A COLUMN OF FLUID IN A TUBE

This application is a division of application Ser. No. 07,462,032, now U.S. Pat. No. 5,099691, filed Jan. 8, 1990.

The invention concerns apparatus for determining in contact-less manner the length of a column of liquid or gaseous substance contained in a tubular cavity closed at one end or open at both, a standing wave of known frequency or wavelength and with known speed of propagation being generated in the column, one node of said standing wave being located at one end of the column, in particular at the closed end opposite the cavity's open end, or an antinode being located at one of the two open ends of the cavity and the frequency of the standing wave being varied.

Heretofore known methods for measuring levels, be it in hydrology, in the zones of surface or of ground waters, in research on computing waste water channels or measuring the level to which reservoirs are filled, all rest predominantly on traditional or costly measurement techniques illustratively employing pressure pickups or floats, or being based on measurements of transit times (echoing).

Aside from the floats used for many years and of which the height function of the level to be measured is sensed by gears, pressure pickups are used which by means of a sensor at their tip measure liquid columns between the pickup tip and the surface of the medium.

Furthermore measurement procedures are used in hydrology that employ stationary systems which by means of pressure-balance at a weighing apparatus determine the height of a water column using a so-called bubble mouthpiece (for instance the compressed air level $\Omega$ made by SEBA Hydrometrie, Kaufbeuren). Again cable-lights sondes and depth probes are being used. As regards the cable-lights sondes, the dipping of a sonde tip into ground water of which the level must be ascertained is being displayed. A length-graduation on the cable allows reading off the height to the water surface. In depth plumbing apparatus, a counter is made to stop when the probe impacts the water surface, and here too the height to the water surface may be determined.

In the known transit-time measurements using echoing, a pulse transmitted by a pulse generator is reflected from the water surface or other object and the time between pulse emission and return for the reflected pulse is taken as the measure of the path covered. Such pulse-echo measurements are hardly used in hydrology because of the expense.

One of the drawbacks of the known mechanical measuring means is that the test values come from inaccurate devices. Besides the inaccuracies due to temperature fluctuations, there are also other difficulties, for instance when inserting floats in plumbing pipes used for ground-water measurements, in particular when these frequently long plumbing pipes are bent.

Temperature-caused inaccuracies also occur in cable-lights sondes and depth-plumbing apparatus. These test devices additionally incur the defect of the elongation of the cable by its own weight. Probes which hang for a long time in water in stationary equipment may become permeable. Again, the probes may tear when being pulled out and hence be lost.

The French patent 2,185,095 describes a procedure to determine the dimensions of test bodies. For that purpose the test bodies are moved into a high-frequency (hf) chamber and two frequencies are ascertained, which are resonant frequencies of the test body of which the dimensions are being sought. On the basis of the equations stated in the French patent 2,185,095 the dimensions of the test body thereupon can be ascertained. An illustrative application provided by the French patent 2,185,095 is the determination of the thermal expansion coefficients of the material making up the test body.

No inference at all can be drawn from the French patent 2,195,085 on how to determine the length of a cavity filled with a gas or liquid by generating a standing wave and ascertaining consecutive maxima (or two minima and one maximum followed by a minimum).

The U.S. Pat. No. 3,237,445 is based on the conventional thickness determination from the equation $t = c/f$ using the resonant frequency of the body's fundamental, where this body's thickness must be ascertained. The U.S. Pat. No. 3,237,445 further states about that known procedure that the resonance frequency is determined by continuously varying the ultrasonic frequency by assuming that the resonant frequency of the fundamental will provide a maximum signal after the ultra-sound has passed through the body being measured (the body is especially transparent to the resonant frequency or the harmonics of same). To avoid changing the frequency until the resonance frequency has been reached, the U.S. Pat. No. 3,237,445 proposes pointing simultaneously ultra-sound with a plurality of frequencies at the test body and to determine the frequencies again after the sound has passed through it. Because the test body is especially transparent to the resonance frequency, the ultra-sound with the resonance frequency will be especially emphasized because that frequency was least damped as it passed through the body.

The British patent 842,241 relates to ultrasonic thickness determination from the equation $f = V/2T$, with the frequency of an oscillator being varied over a predetermined range of the frequency spectrum. At those frequencies where the oscillator responds (harmonic frequency), the half wavelength of the harmonic oscillation is determined and the thickness of the test body is directly read off mutually rotatable scales. The British patent 842,241 cites the presence of standing waves when determining thickness by ultra-sonics.

The German Auslegeschrift 23 12 062 discloses a wall-thickness test means operating on the principle of ultrasonic immersion resonance, an ultrasonic generator being acoustically coupled by a coupling liquid to the object of which it is desired to ascertain the wall thickness. The frequency of the ultrasonic generator is constantly modulated by an hf oscillator whereby transient standing waves are formed in rapid succession in the coupling liquid in many consecutive harmonics (in particular see column 7, lines 46 through column 8, line 6 of the German Auslegeschrift 23 12 062.

The German Auslegeschrift 31 17 236 makes use of a standing wave to ascertain the presence of an object within a monitored space, and whether such an object is moving. The frequency is not changed. No range determination of any kind is performed, rather it must be assumed that the piezoceramic generator of the wave motion is mounted a specific distance from the test body.

As regards the procedure disclosed in the German Auslegeschrift 21 44 472 for measuring the thickness of metal parts, a standing wave is generated between two antennas and the test body is placed between them. The frequency remains constant, and no attempt is made to use the standing waves of which the wavelength changes inside the body to measure this body's thickness.

The object of the present invention is to provide a simple and accurate method for measuring the length of or spacings between the end points of a path to be determined.

This problem is solved in the invention in that the amplitude of the standing wave is determined at that end of the column where the wave is fed in, in that the frequency of the wave is so varied until at least two consecutive maxima (oscillation antinodes), two consecutive minima (nodes) or a minimum following a maximum of the standing wave have been detected, and in that the length of the bar or column is computed using the equation $$L = \sigma c / [2(f_u - f_n)] \quad (3).$$

where L is the length of the column, c is the speed of propagation of the wave, $f_n$ the frequency of the standing wave at the first determined maximum or minimum, $f_u$ the frequency of the standing wave at the last determined maximum or minimum and $\sigma$ is the number of determined maximum or minimum from the nth to the uth maximum or minimum ($\sigma = u - n$), or, if the wavelength $\lambda$ is known, from the equation $$L = \sigma(\lambda_u \lambda_n) / [2(\lambda_n - \lambda u)] \quad (5)$$

where L is the length of the bar or column, $\lambda_n$ the wavelength of the standing wave at the first determined maximum or minimum, $\lambda_u$ the wavelength of the last determined maximum or minimum and o the number of determined maxima or minima from the nth to the uth maximum or minimum ($\sigma = u - n$).

Preferably longitudinal waves are used in the invention.

Preferably a standing acoustic wave shall be generated in the invention in the column.

The invention furthermore applies to the case of generating a standing sound wave in the column, especially for gaseous substances.

In one practical embodiment of the invention, the standing wave in the column is generated from that end where the amplitude of the standing wave is being detected.

Advantageously in practice and for the case of a column containing a tubular cavity sealed at one end, the standing wave shall be generated from the open end of the cavity, or to generate the standing wave a sound generator, illustratively an audio-frequency generator shall be used.

The invention further extends to computing the length of the column of medium at known frequency and wave velocity of the standing wave generated in the column of medium from the formula $$L = c / [2(f_n - f_n - 1)] \quad (1)$$

where L is the length of the column of medium, c the wave velocity, $f_n$ the frequency of the nth maximum and $f_n - 1$ the frequency of the (n−1)th maximum. This is a special case of the computation by formula (3), where $\sigma = 1$.

The invention is superior in accuracy and as regards implementing costs to the known test procedures and is easily digitized.

Another object of the invention is the provision of apparatus with which to carry out a method for determining the length of a column of liquid or gas in a cavity sealed at one end or open at both, and to provide such apparatus of simple design.

This problem is solved by the invention by apparatus characterized by a loudspeaker connected to a spacer of which the other end can be placed against one or the open end of the especially tubular cavity containing the column of gaseous or liquid substance, and by a receiving microphone as an acoustic pickup.

In the case of a column open at both ends, advantageously acoustically absorbing material may be mounted at that end of the column where the standing wave is generated, so that interfering reflection shall be averted.

Further preferred designs of the apparatus of the invention form the objects of the apparatus claims.

The apparatus of the invention is used to couple the sound source required for the sound waves for the measurement of the length of an especially tubular cavity to that cavity. The energization of the gas or liquid column is achieved in such a way that the formation of unambiguous resonances shall be assured so that measurement by the method of the invention can be carried out simply and accurately. The coupling of the transmitted wave is performed by the apparatus of the invention in such manner that the reflected wave can freely exit the entry aperture. Therefore superpositions of the incoming wave with the reflected, standing wave cannot take place. Accordingly any differences in maxima or minima at the receiving microphone that might lead to spurious interpretation are averted.

Further a constant sound volume (acoustic pressure) of the waves generated by the audio generator is assured even when changing the frequency/wavelength in the operation of the apparatus of the invention, if additionally the acoustic pressure shall be measured in the resonance space of the loudspeaker and is fed back through a control circuit and kept constant.

Applications of the apparatus of the invention are the measurement of levels in hydrology and further the fill-condition of reservoirs. Moreover the invention may be used to measure manometric pressure fluctuations and to monitor consumption. The apparatus of the invention operates substantially without mechanical parts and the test values so obtained are at once processable further because already present in digital form. Liquid levels of reservoirs of any liquid, for instance of oil and of liquid gas can be accurately measured and displayed.

Further applications of the invention are in aerodynamics, in meteorology and in vacuum technology, that is, wherever the measurement by manometric liquid columns (for instance mercury columns) is performed.

Because the method and the apparatus of the invention are very accurate, it is possible to determine the quantity of liquid removed from a reservoir by measuring the old and the new levels. In this application the known and complex, mechanical or inductive flow meters can be eliminated.

Illustratively a measurement of the invention is carried out by mounting a sound (audio) generator at the open or at one open end of the pipe and next to it an acoustic receiver (microphone). The sound generator emits sound for instance of known frequency and hence of known wavelength into the pipe. The acoustic receiver continuously senses the acoustic intensity at the open or at one open end of the pipe.

The known frequency (or wavelength) of the sound emitted by the acoustic generator is changed continuously (or stepwise), for instance being increased. As a result, fluctuations of sound intensity arise near the acoustic receiver (microphone). The acoustic intensity is a measure of the standing-wave amplitude. The acoustic intensity always reaches a maximum where there is an antinode of the sound wave produced by the acoustic generator in the pipe near the acoustic receiver (microphone). This is the case if the constant pipe length is one-fourth, three-fourths, five-fourths or seven-fourths, etc. for the unilaterally closed pipe or two-fourths, four-fourths, six fourths or eight-fourths, etc. for the pipe open at both ends, of the wavelength generated each time by the acoustic generator. As a rule, antinodes (amplitude maxima) occur at the open or at one open pipe end if the pipe length (length of the gas or liquid column) is an odd fraction of the four-fold pipe length for the unilaterally closed pipe, or an even fraction for the bilaterally open pipe, of the four-fold pipe length, or, in other words, when the pipe length is an odd four-fold of the quarter-wavelength for the laterally open pipe.

In the measurement method of the invention, the (known) frequency of the acoustic generator is changed and the resonance intensity is ascertained, whereby two consecutive wave amplitudes (antinodes) are then determined. There is no need to know what the number of the maximum is. The sought length of the column of medium at known frequency and wave velocity in the column of medium of the generated standing wave is computed from the equation below $$L = c/[2(f_n - f_{n-1})] \quad (1)$$

where L is the length of the column of medium (in the stated example, the level in the well shaft), c the wave velocity (in the example the sound velocity), $f_n$ the frequency of the nth maximum and $f_{n-1}$ the frequency of the (n−1)th maximum.

Taking into account the speed of sound in air of c = 331.3 + 0.6t m/s, equation (1) may be changed as follows $$L = [331.3 + 0.6t]/[2(f_n - f_{n-1})] \quad (2)$$

where t is the temperature in .C of the medium being measured.

Eq. (1) is derived from the two relations, namely $$L = (2n-1)\lambda_n/4 = (2n-1)c/4f_n \quad (a)$$

for the pipe open at both ends, or $$L = [2n - 1]2\frac{\lambda_n}{4} = \frac{2n-1}{2} \cdot \frac{c}{f_n}$$

for the pipe open at both ends, for the nth maximum, and $$L = [2(n-1)-1]\lambda_{n-1} = (2n-3)c/[4f_{n-1}] \quad (b)$$

for the pipe closed at one end, or $$L = [2(n-1) - 1]2\frac{\lambda_{n-1}}{4} = \frac{2n-3}{2} \cdot \frac{c}{f_{n-1}}$$

for the pipe open at both ends, for the (n−1)th maximum, and where $\lambda_n$ is the wavelength of the nth maximum; $f_n$ is the frequency of the nth maximum; $\lambda_{n-1}$ is the wavelength of the (n−1)th maximum; $f_{n-1}$ the frequency of the (n−1)th maximum; n serial number of the maximum dropping out of the equation and therefore need not be known; c=speed of propagation of the wave in the medium, and L=sought length.

The implementation of the method does not mandatorily require two directly consecutive maxima or minima. Instead maxima or minima also may be used between which there is an arbitrary but known number of maxima or minima.

If the two maxima are not directly consecutive, the length L is computed from $$L = \sigma c/[2(f_u - f_n)] \quad (3)$$

where $\sigma$ is the number of antinodes passed through (neglecting the first); $f_u$ is the frequency of the uth maximum; $f_n$ is the frequency of the nth maximum; $\lambda_u$ is the wavelength of the uth maximum; $\lambda_n$ is the wavelength of the nth maximum; u=the serial number of the last recorded maximum and n=the serial number of the first recorded maximum.

Neither n nor u need be known, however the difference $\sigma = u - n$ must be, that is, it must be counted during measurement, where u should be larger than n, ie, when gradually increasing the frequency, first the nth frequency, then the (n+1)th, then the (n+2)th frequency shall be passed through, etc., and lastly the uth frequency.

If the speed of propagation of the acoustic wave shall be set for air, i.e. C=331.3+0.6t, then $$L = \sigma[331.3 + 0.6t]/[2(f_u - f_n)] \quad (4)$$

Eq. (3) is computed from the two following conditions: last recorded maximum, $L = (2u-1)\lambda_u/4 = (2u-1)c/4f_u$ or $$L = (2u-1)(2\lambda_u)/4 = (2u-1)c/2f_u,$$

first recorded maximum, $L = (2n-1)\lambda_n/4 = (2n-1)c/4f_n$ or $$L = (2n-1)(2\lambda_n)/4 = (2n-1)c/2f_n.$$

If the wavelength and the wave velocity are known, the length can be computed from $$L = \sigma \lambda_u \lambda_n/[2(\lambda_n - \lambda_u)] \quad (5).$$

In eq. (5), L is the length of the column, c the speed of propagation of the wave, $\lambda_n$ the wavelength of the standing at the first ascertained maximum or minimum, $\lambda_u$ the wavelength of the standing wave at the last-determined maximum or minimum and $\sigma$ is the number of ascertained maxima or minima between the uth and the nth maximum or minimum.

The method and/or the apparatus of the invention may also be used to monitor and control the filling of a reservoir. First the level is ascertained in the manner described above. Then the reservoir is filled with the wave emitted into the reservoir, this time at constant frequency. The number of antinodes is ascertained and after the number of antinodes (or of minima) corresponding to the difference between the level determined earlier and that to be reached has been recorded, the filling of the reservoir is stopped.

It was discovered moreover that the receiving microphone of the method and apparatus of the invention need not be mounted precisely at the end of the column. As long as the microphone is mounted within one-eighth of the wavelength outside or inside the column, adequate length measurement shall be possible.

If, in eqs. (3) and (5) $f_n$ is larger than $f_u$ or $\lambda_u$ is larger than $\lambda_n$, then the length shall correspond to the absolute value of the computational result.

Further details of the invention are stated in the description below in relation to the attached drawings.

Figure 4:
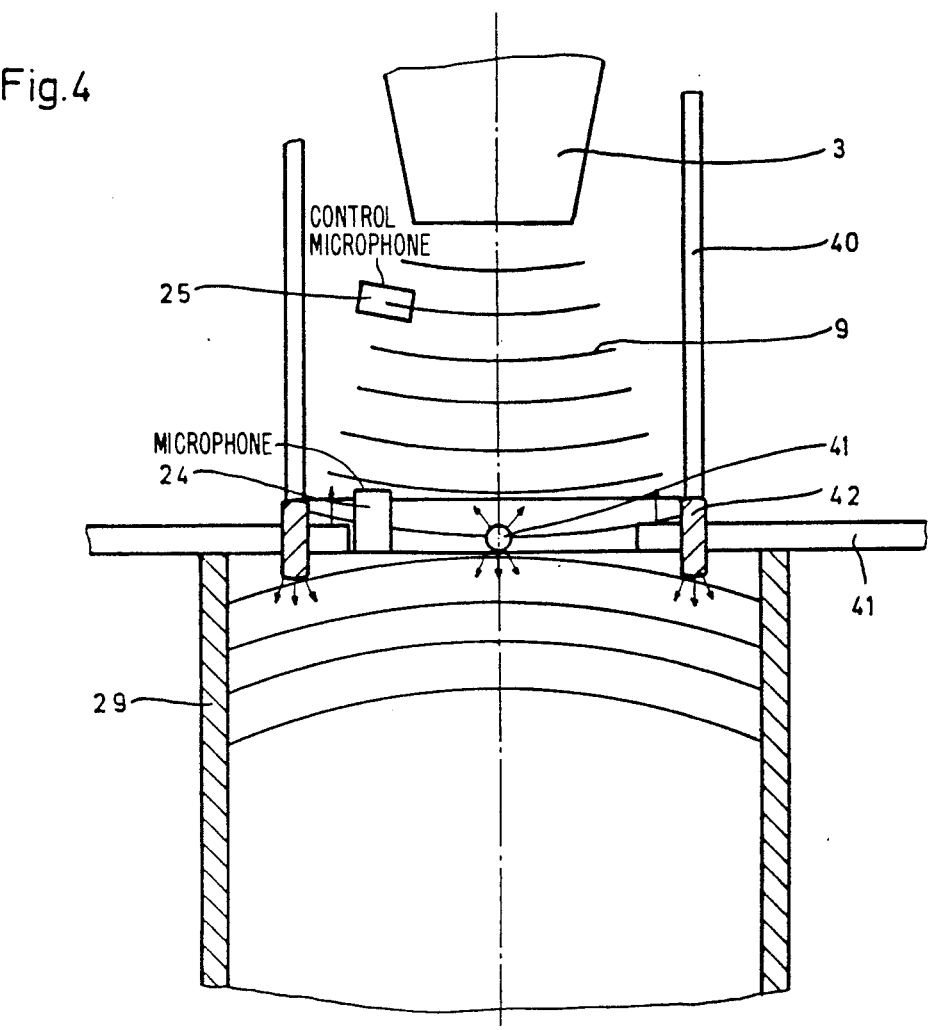
Figure 5:
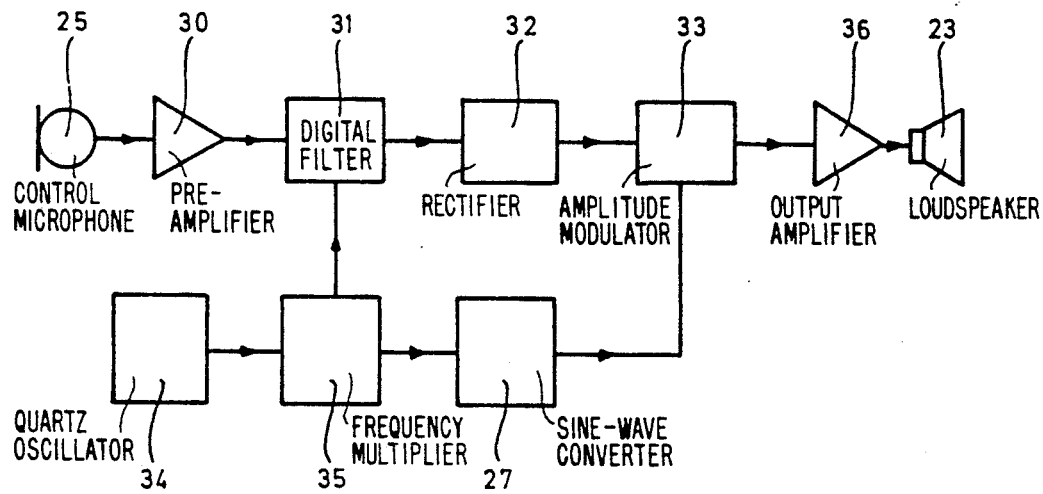
Figure 6A:
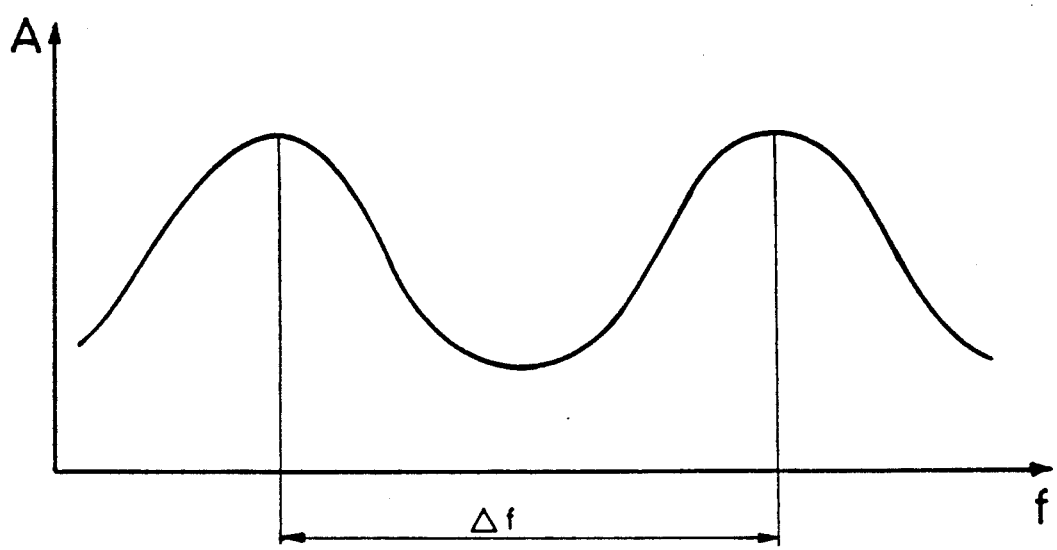
Figure 6B:
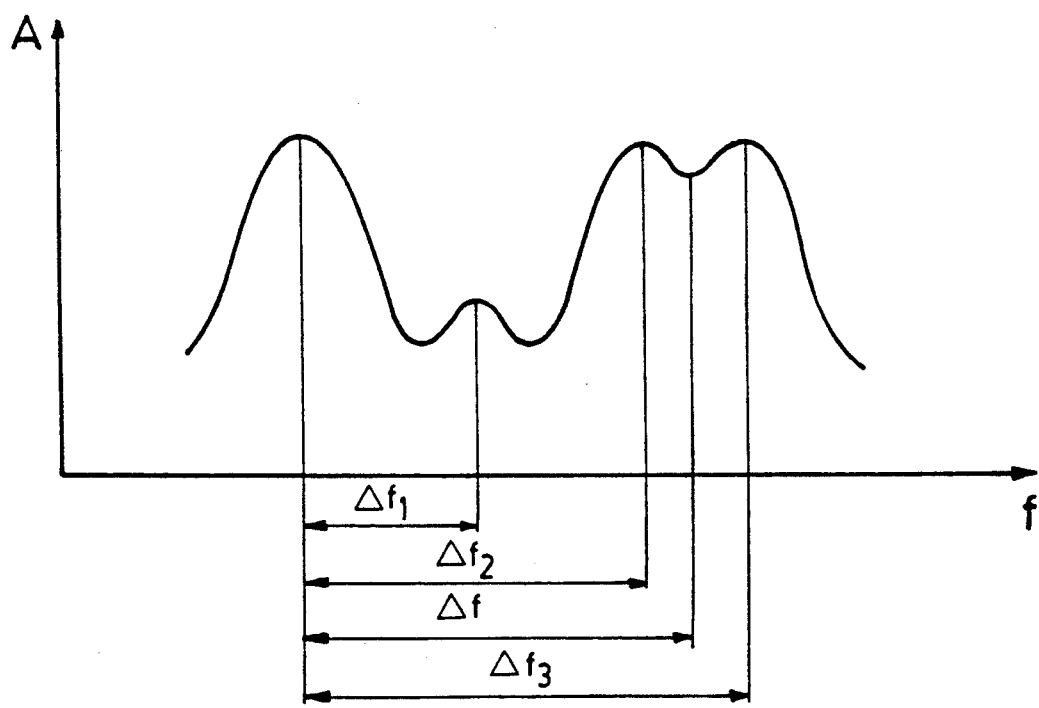
Figure 7:
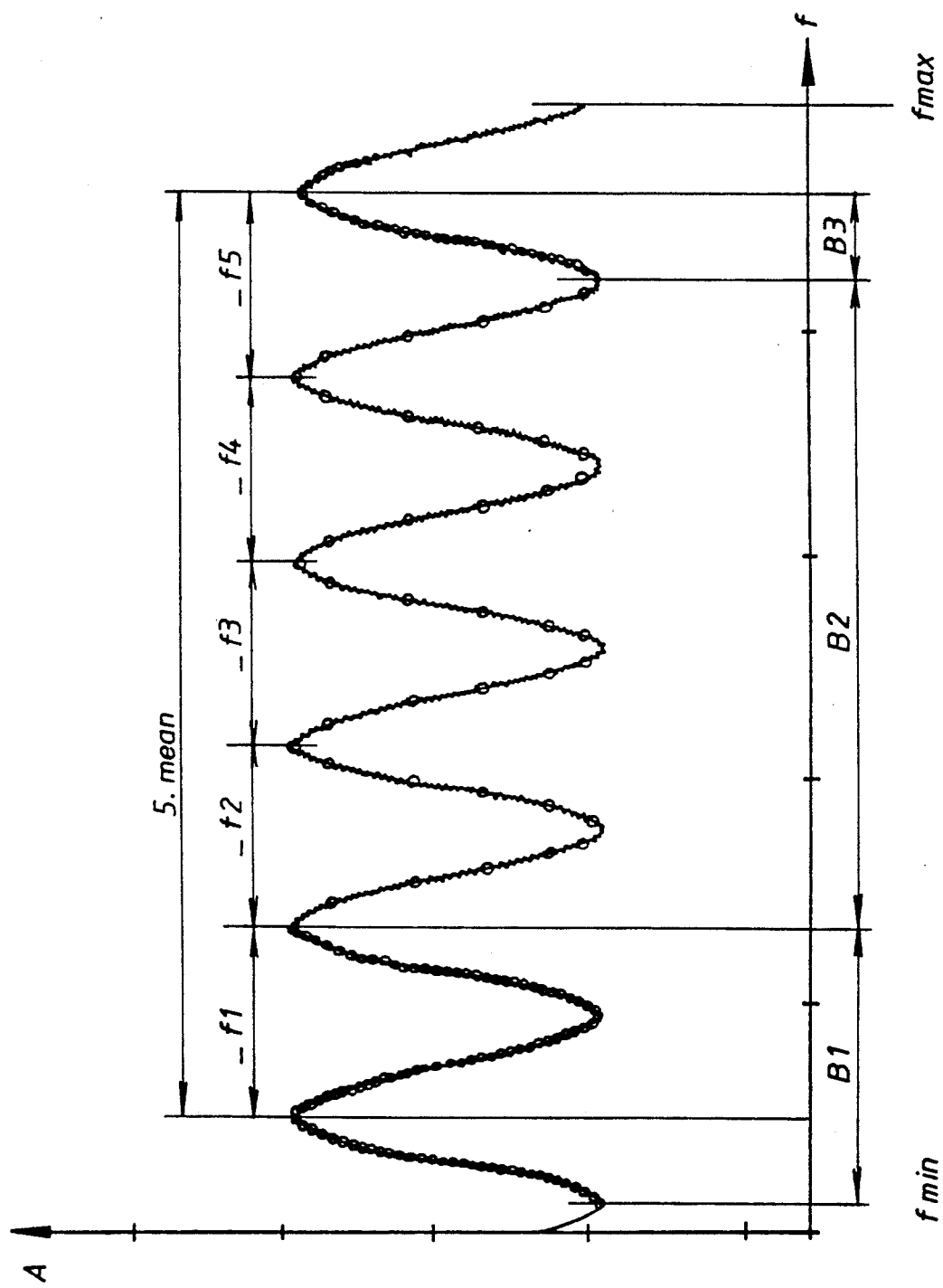

FIGS. 1a and 1b schematically show various standing waves in a column,

FIG. 2 is a functional diagram of the apparatus of the invention,

FIG. 3 is an embodiment mode of the apparatus of the invention set upon a pipe partly filled with liquid, FIG. 4 is a detail of the apparatus of FIG. 3, shown on an enlarged scale, FIG. 5 is a block-circuit diagram of a regulation unit for the apparatus of the invention, FIGS. 6a and 6b show plots of the amplitude A as a function of the frequency f in two different cases, and FIG. 7 is a plot showing the distance between the frequency measurement points.

FIG. 1a illustratively shows standing waves in a pipe 6 of length L, an acoustic (audio) generator 1 and an acoustic receiver (microphone) 7 being associated with the open pipe end. As regards the first example of FIG. 1a, the wavelength $\lambda = 4L$, in the second example, the wavelength $\lambda = 4/3L$, in the third example $\lambda = 4/5L$ and in the fourth $\lambda = 4/7L$.

In general, $\lambda_n = 4L/(2n-1)$, whence $L = (2n-1)\lambda_n/4$.

The examples shown in FIG. 1a each display an antinode at the acoustic generator 1 and a node at the stationary (closed) pipe end.

FIG. 1b shows several examples of standing waves in a bilaterally open pipe 6 of length L, an acoustic generator (audio generator 1), and a sound receiver (microphone 7) being associated with one open pipe end. In the first illustration shown in FIG. 1b, the wavelength $\lambda = 4/2L$, in the second illustration, $\lambda = 4/4L$, in the third illustration $\lambda = 4/6L$ and in the fourth illustration, $\lambda = 4/8L$.

In general, $\lambda_n = 2L/(2n-1)$, and accordingly $$L = (2n-1)\lambda_n/2.$$

FIG. 1b shows that in the examples provided, there is always an antinode both at the sound generator and at the opposite open pipe end.

The amplitude and hence the acoustic intensity at the microphone shall always be a maximum when the wavelength emitted by the acoustic generator shall be an odd fraction of the four-fold length L, namely 4/1, 4/3, 4/5, 4/7 ... etc of the pipe length L, ie when the pipe length is ¼, ¾, 5/4, 7/4 ... etc. of the emitted wavelength, that is, an odd multiple of one fourth the wavelength (FIG. 1a).

Similar considerations apply to FIG. 1b.

The apparatus shown in FIG. 2 is equipped with an acoustic generator in the form of a loudspeaker 1 mounted in a resonance chamber 2 with constricted, tubular acoustic output aperture 3.

The housing of the resonance chamber 2 is provided with a spacer 4 located at the open end 5 of the pipe 6 of which the length L is sought.

An acoustic receiver which in the embodiment is a microphone 7 is also mounted at the open end 5 of the pipe 6. The receiving microphone 7 may be mounted at the part 8 of the spacer 4 resting against the end of the pipe 6.

The design of the spacer 4 is such that the radiation 9 from the reflected wave shall be as unhampered as possible. For that reason the parts of the spacer transverse to the radiation 9 are made narrow. Where called for, the radiated waves may be attenuated further by using damping material.

A control-microphone 10 is mounted in the resonance chamber 2, for instance on its housing. This control microphone 10 is coupled through a regulator 11 to the loudspeaker 1 of which it controls the acoustic output whereby the same acoustic pressure shall be present in the resonance chamber 2 at every frequency (wavelength).

The apparatus employed to implement the method of the invention may be programmed in such manner that it shall operate in part or in whole fully automatically so that the operator need only read off the result, i.e. the sought length.

The apparatus of FIG. 3 consists of a housing 21, a spacer 22 (comprising a spacing stub 40, support rods 41 and fastener ring 42), a loudspeaker 23, a receiving microphone 24, a control microphone 25, a regulator unit 26 and a sinewave generator 27.

The shape of the housing 21 at the acoustic exit is selected in such a way that the reflected wavefront 9 no longer can be reflected back into the pipe 29. Here again additional damping material may be provided to prevent reflections.

The purpose of the spacer 22 is to keep the loudspeaker 23 away from the open end of the pipe 29 and to hold the receiver microphone 24 at the pipe aperture. The components of the spacer 22, in particular its support rods 41, are designed in such a way that as little as possible of interfering radiation (indicated by arrows in FIG. 4) is generated in the transmitted and reflected wavefront 9. Advantageous geometries are round rods and rings with round end surfaces, as shown in detail also in FIG. 4.

The regulator unit 26 consists of the control microphone 25, a pre-amplifier 30, a digital filter 31 of which the pass frequency is within the transmitted frequency, a rectifier 32, an amplitude modulator 33, an output amplifier 36, a quartz oscillator 34, a frequency multiplier 35 which also clocks the filter 31, and a square-pulse/sine-wave converter 27. The block-circuit diagram of the regulator unit is shown in FIG. 5.

FIG. 6a shows the amplitude A of the standing wave at one or at the open end of the pipe 6 or 29 as a function of the frequency f. The measurement accuracy depends on the precision with which the maxima or minima can be spotted. The maxima shown in FIG. 6a are unambiguously measurable and therefore provide an accurate result. The accuracy furthermore depends directly on the number of maxima or minima in the measurement range. The more maxima or minima are being measured, the smaller the significance of the percentage error involved in spotting maxima or minima.

FIG. 6b shows a case wherein the amplitude A is degraded by additional reflections. The maximum following Δf1 occurs when reflections take place causing an increase in sound volume. The drop in sound volume following Δf may occur on account of reflection from the housing or through inappropriate coupling.

The apparatus of the invention offers high accuracy and reliability of measurement. The following are among the advantageous factors:

(a) The design of the housing and of the spacer is such that no additional reflections occur (FIGS. 3, 4); where called for, damping materials may be applied when using pipes open at both ends, (b) The coupling level of the transmitted waves is kept constant over the entire range of frequencies, (c) The highest sensitivity of the control and of the receiving microphone is at the transmission frequency to eliminate environmental noise.

FIG. 7 shows the amplitude A of the standing wave at the or one open end of the pipe 6 and 29 resp. as a function of the frequency f. The sampling of the measurement frequency is much tighter in the initial and final ranges B1 and B3 than in the center range B2. Thereby the distance $f_1$ between the first and second maxima and also the sixth maximum can be ascertained more accurately and the measurement as a whole is thus more accurate.

The method of the invention can be optimized as follows regarding accuracy and measurement time. The problem is to reliably determine under all conditions the mean distance Δf (FIG. 6a) between consecutive maxima and minima.

Regarding FIG. 7, the method of the invention can be carried out as follows:

(a) DETERMINING THE MAXIMUM MEASUREMENT FREQUENCY

The wavelength at the maximum frequency must be large compared to the pipe diameter because otherwise no standing wave shall form in the pipe.

(b) DETERMINING THE SAMPLING DISTANCE dF OF THE MEASUREMENT FREQUENCY

It is determined by the greatest of the lengths to be measured. The minimum frequency difference occurs between the beat maxima or minima. For good analysis, at least 12 frequency points shall be measured between two maxima or minima.

$dF \leq c/[12(2L_{max})]$ (=minimum frequency difference).

(c) AWAITING ONSET OF OSCILLATION

A waiting period is mandatory between setting the frequency and scanning the sound volume at least until the wave reflected at the pipe end has come back to the input, in other words the waiting time is $dt \geq 2L_{max}/c.$

(d) LOWEST FREQUENCY AT BEGINNING OF MEASUREMENT

The minimum frequency at which an extremum may yet occur is given by $f_{min} = c/(4L_{min}).$ Accordingly there is little point in starting to measure at much below that frequency.

(e) PROCEEDING WITH THE MEASUREMENT

— Start with lowest frequency at minimum sampling distance dF and longest waiting time dt, — Increase the frequency in increments of dF until the first and second minimum or maximum occurs, — A first estimate of pipe length can be obtained from the frequency difference between the two minima/maxima and accordingly the waiting time and frequency distance can be matched to the expected pipe length, in other words, henceforth:

I. On the basis of the initially coarsely predicted pipe length, the waiting time can be set to the particular shortest predictable value, and II. dF is so enlarged that the fewest measurements ≧ 12 will be located between two consecutive maxima or minima.

III. The required number of maxima or minima which must be ascertained depends on the one hand on the required accuracy and on the other on the available time for measurement. The largest possible number of maxima or minima (within the admissible measurement range of I and II) must be ascertained to achieve highest accuracy. If the measurement times are limited or if the accuracy requirement is not so great, the number of maxima or minima to be ascertained can be lowered to the theoretical limit value of two consecutive maxima or minima.

IV. Because the measurement accuracy depends directly on how accurately Δf is determined, advantageously at the end of the measurement interval the least frequency difference of the frequency distance dF shall be reverted to (FIG. 7).

V. Measurement also may begin at the highest frequency and be carried out with step-wise lowering of the frequency. All implementations then must be adapted correspondingly.

What is claimed is:

1. Apparatus for measuring the length of a column of fluid in a tube, comprising a resonance chamber, a loudspeaker mounted in the resonance chamber, the resonance chamber having a constricted tubular acoustic exit aperture, a spacer adapted to rest against an open end of said tube and to position said resonance chamber relative to said tube such that said constricted acoustic exit aperture of said resonance chamber is spaced a substantial distance from said open end of said tube and is directed towards said open end of said tube, and a microphone carried by said spacer in a position such that when said spacer rests against said open end of said tube, said microphone is at said open end of said tube and said loudspeaker is spaced from said open end of said tube a distance greater than said substantial distance, the loudspeaker generating in the tube a standing wave having nodes and antinodes and the microphone measuring said nodes or antinodes to determine said length.

2. Apparatus according to claim 1, and means for varying the maximum sensitivity of said microphone thereby to adapt the maximum sensitivity of the microphone to the frequency of sound emitted by the loudspeaker.

3. Apparatus according to claim 1, said spacer comprising a ring connected by rods to said resonance chamber, said ring having supporting rods extending partway radially into the interior of the ring whereby said supporting rods can rest on said open end of the tube with the ring surrounding the open end of the tube.

4. Apparatus according to claim 1, said spacer comprising a ring connected by rods to said resonance chamber, said ring having supporting rods projecting radially outwardly beyond said ring whereby said supporting rods can rest on said open end of the tube with the ring disposed within the open end of the tube.

5. Apparatus according to claim 1, wherein said constricted tubular acoustic exit aperture is conical and converges toward said open end of said tube.

6. Apparatus according to claim 1, said spacer having surfaces facing said open end of the tube that are of convex curvature.

7. Apparatus according to claim 1, there being a detector of acoustic pressure in said resonance chamber, and control means for controlling said loudspeaker according to a detection by said detector thereby to maintain the acoustic pressure in the resonance chamber constant despite variations of frequency of sound emitted by said loudspeaker.

* * * * *